United States Patent
Zhuang et al.

(10) Patent No.: US 12,220,210 B2
(45) Date of Patent: Feb. 11, 2025

(54) CARDIAC PHYSIOLOGICAL PARAMETER MEASURING METHOD, DEVICE, TERMINAL AND COMPUTER STORAGE MEDIUM

(71) Applicant: SHENZHEN DARMA TECHNOLOGY CO., LTD., Shenzhen (CN)

(72) Inventors: Shaochun Zhuang, Shenzhen (CN); Fei Ye, Shenzhen (CN); Yeping Li, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 988 days.

(21) Appl. No.: 17/256,222

(22) PCT Filed: Jun. 27, 2018

(86) PCT No.: PCT/CN2018/093168
§ 371 (c)(1),
(2) Date: Dec. 27, 2020

(87) PCT Pub. No.: WO2020/000268
PCT Pub. Date: Jan. 2, 2020

(65) Prior Publication Data
US 2021/0169350 A1    Jun. 10, 2021

(51) Int. Cl.
*A61B 5/02*   (2006.01)
*A61B 5/00*   (2006.01)
*A61B 5/024*  (2006.01)

(52) U.S. Cl.
CPC ...... *A61B 5/02028* (2013.01); *A61B 5/02444* (2013.01); *A61B 5/6813* (2013.01); *A61B 5/742* (2013.01)

(58) Field of Classification Search
CPC ... A61B 5/742; A61B 5/6813; A61B 5/02444; A61B 5/02028
See application file for complete search history.

(56) References Cited

U.S. PATENT DOCUMENTS

| | | | | |
|---|---|---|---|---|
| 6,480,733 B1 * | 11/2002 | Turcott | ........ | A61B 5/0002 600/509 |
| 2005/0222515 A1 * | 10/2005 | Polyshchuk | ........ | A61B 7/04 600/528 |

(Continued)

FOREIGN PATENT DOCUMENTS

| CN | 101951831 A | 1/2011 |
|---|---|---|
| CN | 105326477 A | 2/2016 |

(Continued)

*Primary Examiner* — Lynsey C Eiseman
*Assistant Examiner* — Amanda L Steinberg
(74) *Attorney, Agent, or Firm* — Cheng-Ju Chiang

(57) ABSTRACT

A cardiac physiological parameter measuring method, a device, a terminal and a computer storage medium, comprising: by means of one or more vibration sensors, acquiring vibration information of a subject to be tested that is in a supine state, the vibration sensors being configured to be disposed below the left shoulder of the subject to be tested; generating hemodynamic related information on the basis of the vibration information determining an MC feature point of an MC event on the basis the hemodynamic related information.

9 Claims, 9 Drawing Sheets

(56) References Cited

U.S. PATENT DOCUMENTS

| | | | | |
|---|---|---|---|---|
| 2011/0028855 A1* | 2/2011 | Blomqvist | | A61B 5/053 |
| | | | | 600/509 |
| 2011/0152638 A1* | 6/2011 | Bartnik | | G16H 50/70 |
| | | | | 600/301 |
| 2011/0263994 A1* | 10/2011 | Burns | | A61B 5/339 |
| | | | | 600/509 |
| 2011/0295127 A1* | 12/2011 | Sandler | | A61B 5/318 |
| | | | | 600/528 |
| 2014/0070957 A1* | 3/2014 | Longinotti-Buitoni | | |
| | | | | A61B 5/02055 |
| | | | | 340/870.01 |
| 2016/0089031 A1* | 3/2016 | Hu | | A61B 5/1116 |
| | | | | 600/479 |
| 2017/0119255 A1 | 5/2017 | Mahajan et al. | | |
| 2017/0188866 A1* | 7/2017 | Kale | | A61B 5/0044 |
| 2019/0046064 A1* | 2/2019 | Centen | | A61B 5/282 |
| 2020/0046241 A1* | 2/2020 | Lam | | A61B 5/318 |

FOREIGN PATENT DOCUMENTS

| | | |
|---|---|---|
| CN | 105491942 A | 4/2016 |
| CN | 108057176 A | 5/2018 |

\* cited by examiner

CARDIAC PHYSIOLOGICAL PARAMETER MEASURING METHOD, DEVICE, TERMINAL AND COMPUTER STORAGE MEDIUM

CROSS REFERENCE TO RELATED APPLICATIONS

The present application is a 35 U.S.C. § 371 National Phase conversion of International (PCT) Patent Application No. PCT/CN2018/093168, filed on Jun. 27, 2018, the disclosure of which is incorporated by reference herein. The PCT International Patent Application was filed and published in Chinese.

FIELD OF THE INVENTION

The present invention relates to the field of cardiac physiological parameter measurement, and particularly relates to a cardiac physiological parameter measuring method, a device, a terminal and a computer storage medium.

BACKGROUND OF THE INVENTION

Commonly used methods of cardiac function detection to obtain parameters are generally divided into two ways: methods on the basis of traumatic detection and methods on the basis of non-invasive detection.

Where the methods on the basis of traumatic detection to obtain parameters include: cardiac catheterization, such as coronary angiography to obtain cardiac physiological parameters; these methods on the basis of traumatic detection to obtain parameters likely cause harm to the tested subject, and cannot repeat the detection multiple times. Methods on the basis of non-invasive detection include methods of generating ECG/PCQ etc. These detection methods need to attach a sensor at a designated position on the human skin.

A more convenient and comfortable method for measuring cardiac parameters is needed.

SUMMARY OF THE INVENTION

Accordingly, the present invention provides a cardiac physiological parameter measuring method, a device, a terminal and a computer storage medium. The cardiac physiological parameter measuring method provided can be performed by a subject lying down.

The present invention proposes the following specific embodiments:

A cardiac physiological parameter measuring method provided in accordance with the embodiments of the present invention, comprising steps of:
    acquiring vibration information of a subject to be tested in a supine state by means of one or more vibration sensors; wherein the one or more vibration sensors are configured to be disposed below the left shoulder of the subject to be tested;
    generating hemodynamic related information on the basis of the vibration information; and
    determining an MC feature point of an MC event on the basis the hemodynamic related information.

In a specific embodiment, the vibration sensor is selected from one or more of: an acceleration sensor, a speed sensor, a displacement sensor, a pressure sensor, a strain sensor, a stress sensor, or sensors that convert physical quantities equivalently on the basis of acceleration, speed, pressure, or displacement.

In a specific embodiment, the strain sensor is a fiber-optic sensor.

In a specific embodiment, the vibration sensor is configured to be disposed below the left shoulder blade of the subject to be tested.

In a specific embodiment, a sensing area of the vibration sensor covers the back area corresponding to the left shoulder blade of the subject to be tested.

In a specific embodiment, the step of "generating hemodynamic related information on the basis of the vibration information" comprises:
    generating hemodynamic related information by preprocessing the vibration information, where the preprocessing comprises at least one of: filtering, denoising, and signal scaling.

In a specific embodiment, the step of "determining an MC feature point of an MC event on the basis the hemodynamic related information" further comprises steps of:
    graphically displaying the hemodynamic related information;
    determining a point of manual calibration on the graphical display interface; and
    setting the point as the MC feature point of the MC event.

In a specific embodiment, the method further includes: displaying prompt information on the graphical display interface; wherein, the prompt information is used to prompt manual calibration of the MC feature point of the MC event.

In a specific embodiment, the step of "determining an MC feature point of an MC event on the basis the hemodynamic related information" comprises:
    determining an MC feature point of an MC event from the hemodynamic related information on the basis of a feature search.

In a specific embodiment, the step of "determining an MC feature point of an MC event on the basis the hemodynamic related information" further comprises steps of:
    extracting high-frequency component from the hemodynamic related information to obtain a high-frequency component signal waveform graph; and
    performing a feature search on the high-frequency component signal waveform graph to determine the MC feature point of the MC event.

In a specific embodiment, the step of "extracting high-frequency component from the hemodynamic related information" includes:
    extracting high-frequency component from the hemodynamic related information by means of polynomial fitting and smooth filtering.

In a specific embodiment, the step of "determining an MC feature point of an MC event on the basis the hemodynamic related information" further comprises steps of:
    performing second-order differential processing and fourth-order differential processing on the hemodynamic related information to generate a second-order differential graph and a fourth-order differential graph, respectively;
    setting the highest peak in one cardiac cycle of the second-order differential graph as an auxiliary feature point;
    synchronizing the second-order differential graph and the fourth-order differential graph on the same time axis, and determining a time point on the fourth-order differential graph corresponding to the auxiliary feature point on the second-order differential graph; and determining the first valley on the fourth-order differential graph before the time point in the same cardiac cycle as the MC feature point of the MC event.

In a specific embodiment, the method further comprises a step of:

determining an AVO feature point of an AVO event on the basis the hemodynamic related information.

In a specific embodiment, the step of "determining an AVO feature point of an AVO event on the basis the hemodynamic related information" further comprises steps of:

graphically displaying the hemodynamic related information; and displaying prompt information on the graphical display interface; wherein the prompt information is used to prompt manual calibration of the AVO feature point of the AVO event;

determining a point of manual calibration on the graphical display interface; and setting the point as the AVO feature point of the AVO event.

In a specific embodiment, "determining an AVO feature point of an AVO event on the basis the hemodynamic related information" further comprises steps of:

performing second-order differential processing on the hemodynamic related information to generate a second-order differential graph; and determining the highest peak in one cardiac cycle of the second-order differential graph as the AVO feature point of the AVO event.

In a specific embodiment, the method further comprises a step of:

determining IVCT on the basis of the time points corresponding to the MC feature point and the AVO feature point in the same cardiac cycle.

In a specific embodiment, the step of "determining IVCT on the basis of the time points corresponding to the MC feature point and the AVO feature point in the same cardiac cycle" further comprises steps of:

determining MC time points corresponding to MC feature points and AVO time points corresponding to AVO feature points in multiple cardiac cycles;

determining the IVCT in each cardiac cycle on the basis of the MC time point and the AVO time point in the same cardiac cycle; and averaging the IVCT in each cardiac cycle to obtain the final IVCT.

In a specific embodiment, the method further comprises steps of:

performing peak search on the signal waveform corresponding to hemodynamic related information; and setting the time interval corresponding to the waveform between the two adjacent highest peaks as one cardiac cycle.

In a specific embodiment, the method further comprises steps of:

while acquiring vibration information of a subject to be tested in a supine state by means of one or more vibration sensors, acquiring a synchronous monitoring electrocardiogram of the subject to be tested; and determining the cardiac cycle on the basis of the synchronous monitoring electrocardiogram.

In a specific embodiment, the method further comprises steps of:

while acquiring vibration information of a subject to be tested in a supine state by means of one or more vibration sensors, acquiring PCG signals of the apex region of the subject to be tested;

determining the MC feature point of the MC event and the AVO feature point of the AVO event on the basis of the graph corresponding to the PCG signals; and using the MC feature point and/or AVO feature point obtained by the PCG signals to correct the MC feature point and/or AVO feature point obtained by the feature search method using the vibration information.

In a specific embodiment, the vibration sensors are not in direct contact with the subject to be tested.

In a specific embodiment, the method further comprises a step of:

outputting one or more of: the information of the MC feature point, the information of the AVO feature point, and the IVCT.

The embodiment of the present invention also provides a cardiac physiological parameter measuring device, which comprises:

an acquisition unit, for acquiring vibration information of a subject to be tested in a supine state by means of one or more vibration sensors; wherein the one or more vibration sensors are configured to be disposed below the left shoulder of the subject to be tested;

a generating unit, for generating hemodynamic related information on the basis of the vibration information; and a determining unit, for determining an MC feature point of an MC event on the basis the hemodynamic related information.

The embodiment of the present invention also provides a terminal, which comprises:

a processor; and a memory storing instructions executable by the processor;

wherein the processor is used to perform:

acquiring vibration information of a subject to be tested in a supine state by means of one or more vibration sensors; wherein the one or more vibration sensors are configured to be disposed below the left shoulder of the subject to be tested;

generating hemodynamic related information on the basis of the vibration information; and determining an MC feature point of an MC event on the basis the hemodynamic related information.

The embodiment of the present invention also provides a computer storage medium that stores computer program, and the computer program are executed to perform the following processes:

process A: acquiring vibration information of a subject to be tested in a supine state by means of one or more vibration sensors; wherein the one or more vibration sensors are configured to be disposed below the left shoulder of the subject to be tested;

process B: generating hemodynamic related information on the basis of the vibration information; and process C: determining an MC feature point of an MC event on the basis of the hemodynamic related information.

The embodiment of the present invention also provides a cardiac physiological parameter measuring system, comprising: one or more vibration sensors and an information processing device;

wherein the one or more vibration sensors are used for acquiring vibration information of a subject to be tested in a supine state; the one or more vibration sensors are configured to be disposed below the left shoulder of the subject to be tested; and the information processing device is used for obtaining the vibration information collected by the one or more vibration sensors, generating hemodynamic related information on the basis of the vibration information; and determining an MC feature point of an MC event on the basis the hemodynamic related information.

BRIEF DESCRIPTION OF THE DRAWINGS

In order to explain the technical solutions of the embodiments of the present invention more clearly, the following will briefly introduce the drawings needed in the embodiments. It should be understood that the following drawings only show certain embodiments of the present invention, and therefore should not be regarded as a limitation of the scope. For those of ordinary skill in the art, other related drawings can be obtained from these drawings without creative work.

DETAILED DESCRIPTION OF THE INVENTION

Hereinafter, various embodiments of the present invention will be described more fully. The present invention may have various embodiments, and adjustments and changes may be made therein. However, it should be understood that there is no intention to limit the present invention to the specific embodiments disclosed herein, but the present invention should be understood to cover all adjustments, equivalents and/or alternatives within the spirit and scope of various embodiments of the present invention.

The terms used in various embodiments of the present invention are only used for the purpose of describing specific embodiments and are not intended to limit various embodiments of the present invention. As used herein, the singular form is intended to also include the plural form, unless the context clearly states. Unless otherwise defined, all terms (including technical and scientific terms) used herein have the common meanings as being understood by those of ordinary skill in the art which the embodiments of the present invention belong to. The terms (such as those defined in commonly used dictionaries) will be interpreted according to the contextual in the related technical field and will not be interpreted as idealized or overly formal meanings, unless clearly defined in the embodiments of the present invention.

Embodiment 1

The embodiment of the present invention provides a cardiac physiological parameter measuring method for obtaining cardiac physiological parameters.

Figure 1:
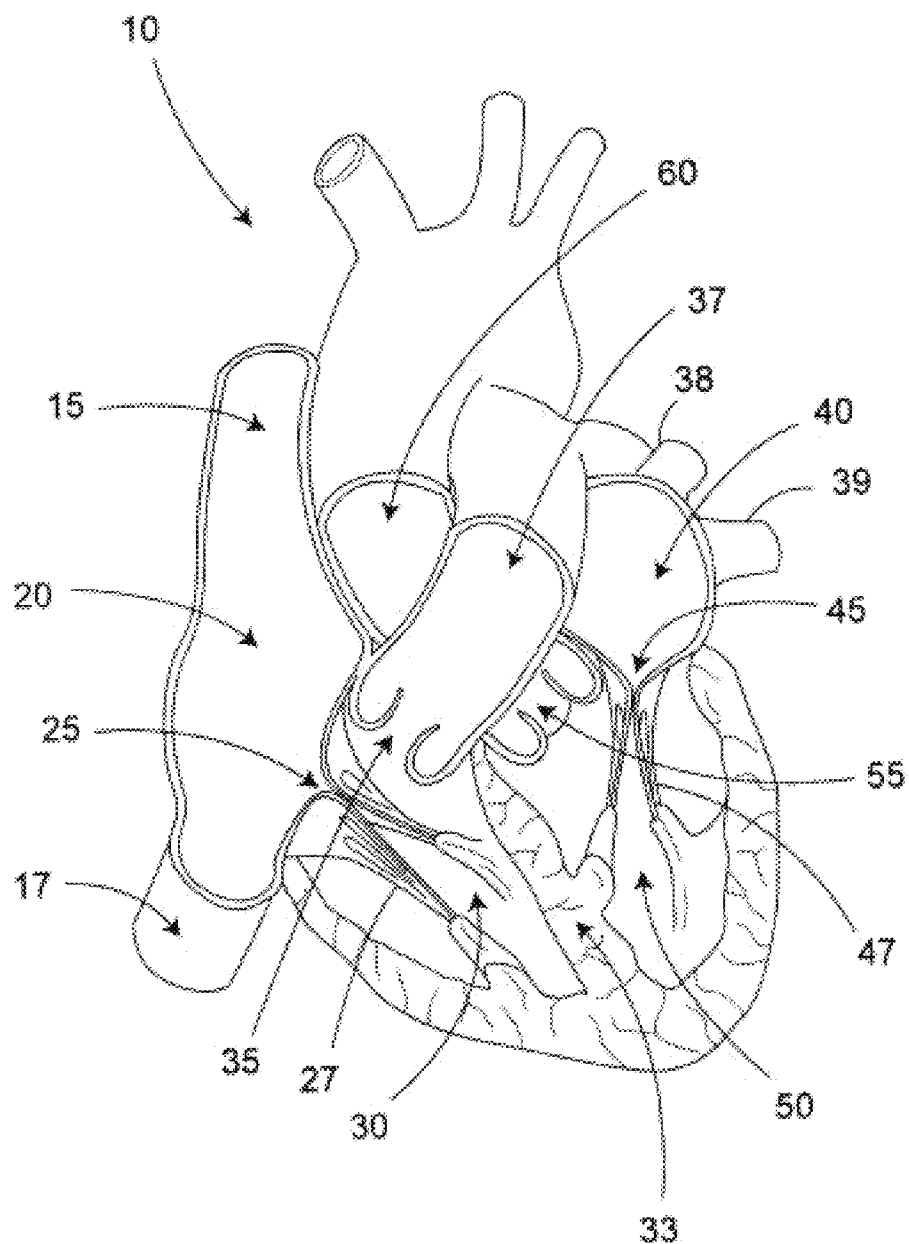
FIG. 1 is a schematic diagram illustrating the heart structure in accordance with an embodiment of the present invention.

As shown in FIG. 1, the heart structure and the mechanical process of heart beat are as follows: the heart 10 includes four chambers, the right atrium 20 and the right ventricle 30 that are connected to each other through the tricuspid valve 25, and the left atrium 40 and the left ventricle 50 that are connected to each other through the mitral valve 45. The blood flows back to the right atrium 20 via the superior vena cava 15 from the upper half of the body and via the inferior vena cava 17 from the lower half of the body. The myocardium of the right atrium 20 and the papillary muscle 27 of the right ventricle 30 simultaneously contract to open the tricuspid valve 25, so that blood can flow from the right atrium 20 into the right ventricle 30, and then the tricuspid valve 25 closes when the papillary muscle 27 relaxes. When the myocardium of the right ventricle 30 contracts, blood flows from the right ventricle 30 through the pulmonary valve 35 (labeled to both sides of the valve rather than the hole) into the pulmonary artery 37, which transports the blood to the lungs, where the blood is oxidized. The oxidized blood returns to the left atrium 40 through the pulmonary veins 38 and 39. The myocardium of the left atrium 40 and the papillary muscle 47 of the left ventricle 50 contract simultaneously, the mitral valve 45 opens so that oxidized blood flows from the left atrium 40 into the left ventricle 50, and then the papillary muscle 47 relaxes to allow the mitral valve 45 to close. Then, the left ventricle 50 compresses the oxidized blood to flow through the aortic valve 55 to enter the aorta 60, and the aorta 60 delivers the oxidized blood to the entire body via the peripheral vascular system.

The cyclical beating of the heart will cause various periodic changes, such as intracardiac pressure and cardiovascular pressure, the volume of the atria and ventricles, periodic changes in opening and closing of intracardiac valves (including mitral valve, tricuspid valve, aortic valve, pulmonary valve), and blood flow speed, etc. These changes drive blood to flow in a certain direction in the blood vessel. Hemodynamics studies dynamics of blood flow in the cardiovascular system, which aims to blood flow and blood vessel wall deformation. The "hemodynamic related information" described in this invention refers to any hemodynamic related information, which can include, but not limited to, one or more of: information related to blood flow generation (for example, heart's ejection caused by the contraction and relaxation of the heart), and blood flow-related information (such as cardiac output CO, left ventricular ejection impacting the aortic arch), blood pressure-related information (such as systolic arterial pressure, diastolic blood pressure, mean arterial pressure), or blood vessel-related information (for example, vascular elasticity). The cyclical beating of the heart can maintain blood circulation. Therefore, various parameters related to the beating of the heart, such as opening and closing of the intracardiac valve, changes in the volume of the atria and ventricles, etc., are all hemodynamic related information.

This invention discloses a method: measuring the vibration information of the human body; obtaining hemodynamic related information from the vibration information of the human body, and then obtaining the required vital sign information (for example, various parameters for the heartbeat) from the hemodynamic related information. Therefore, in accordance with this invention, acquire vibration information of the body using an information acquisition device first, and then extract hemodynamic related information from the vibration information (including cardiac vibration information and some information about blood flow).

And then, extract the MC (Mitral Valve Closure, also abbreviated as MVC) feature point and the AVO (Aortic Valve Opening) feature point from the hemodynamic related information.

Figure 2:
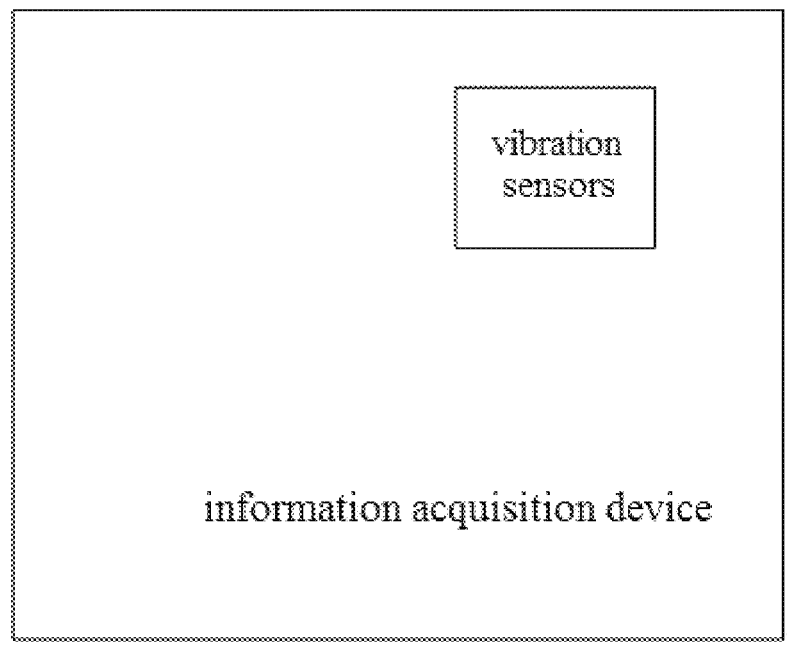
FIG. 2 is a schematic diagram of an information acquisition device in accordance with the embodiment of the present invention.

FIG. 2 shows a schematic diagram of an information acquisition device. The information acquisition device may include one or more vibration sensors, where each vibration sensor can be individually switched for data collection in a combination of multiple different vibration sensors; for example, only turning on one vibration sensor corresponding to the left shoulder of the subject to be tested for data collection.

The location of each vibration sensor corresponds to different sections of the human body, and further, the vibration sensor may comprise any one or more combination selected from: an acceleration sensor, a speed sensor, a displacement sensor, a pressure sensor, a strain sensor, a stress sensor, or sensors (such as electrostatic sensors, inflatable micro-motion sensors, radar sensors, etc.) that convert physical quantities equivalently based on acceleration, speed, displacement, or pressure. The strain sensor may be a fiber-optic strain sensor. The information acquisition device as shown in FIG. 2 includes a vibration sensor. When the information acquisition device collects human body' vibration information, the subject to be tested needs to lie on its back on the information acquisition device, and the vibration sensor is configured to be disposed below the left shoulder of the subject to be tested. In some embodiments, the information acquisition device can also be implemented on a chair or other seating equipments. Specifically, the information acquisition device can be placed on a chair seat for the subject to sit on, or placed on the back of a chair for the subject to lean against.

Specifically, the vibration sensors may not directly contact the subject to be tested.

Figure 3:
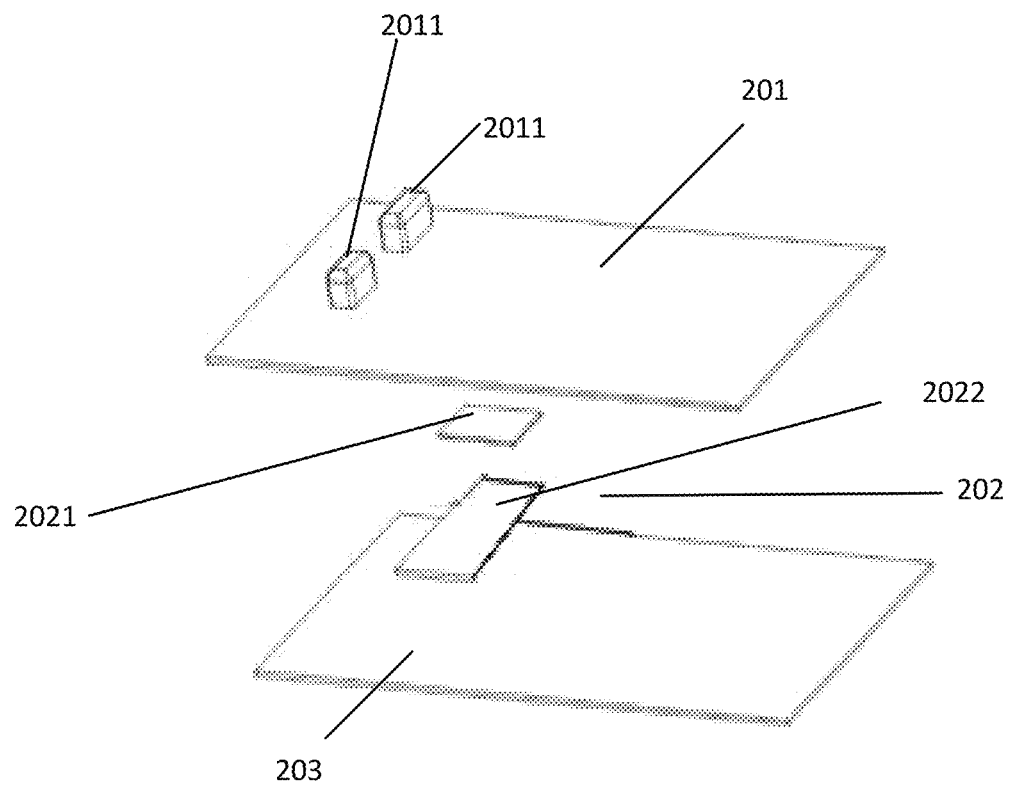
FIG. 3 is a schematic structural diagram of the information acquisition device in accordance with the embodiment of the present invention.

In some embodiments, the information acquisition device can be a cushion (as shown in FIG. 3), the vibration sensor can be a fiber-optic sensor, and the subject to be tested needs to lie flat on it in a supine resting state. In a layered view as shown in FIG. 3, a middle layer 202 includes a sensor 2021 and a supporting structure 2022. The sensor 2021 can be a fiber-optic sensor. The fiber-optic sensor has high sensitivity and can capture micro vibrations of the body. When the tester lies down, his shoulder is correspondingly disposed on the sensor. In some embodiments, the support structure 2022 supports under the sensor 2021 for the sensor rebounding, and the support structure 2022 may be a layer of rigid plate. An upper layer 201 and a lower layer 203 are used as jackets for encapsulating the sensor 2021 and the supporting structure 2022. The upper layer 201 can also be provided with a positioning mark 2011, so that the tester can lie down on the test position accurately and quickly. The specific positioning mark 2011 can be a shoulder block, a neck pillow, or a foot block, a body contour, etc, and any mark as long as obviously indicating the subject to quickly lie on a predetermined position, can be used as the positioning mark 2011.

The principle of the fiber-optic sensor measuring body vibration is: when an external force is applied to the fiber-optic sensor, for example, when the human body lies flat on the cushion in a resting state, the human body's breathing and heartbeat will cause micro vibrations of the body. Micro vibration can make the bending of the optical fiber, which will change the parameters of light passing through the optical fiber, for example, changes in intensity of light. The changes in intensity of light after processing can be used to represent the body vibration.

Figure 4:
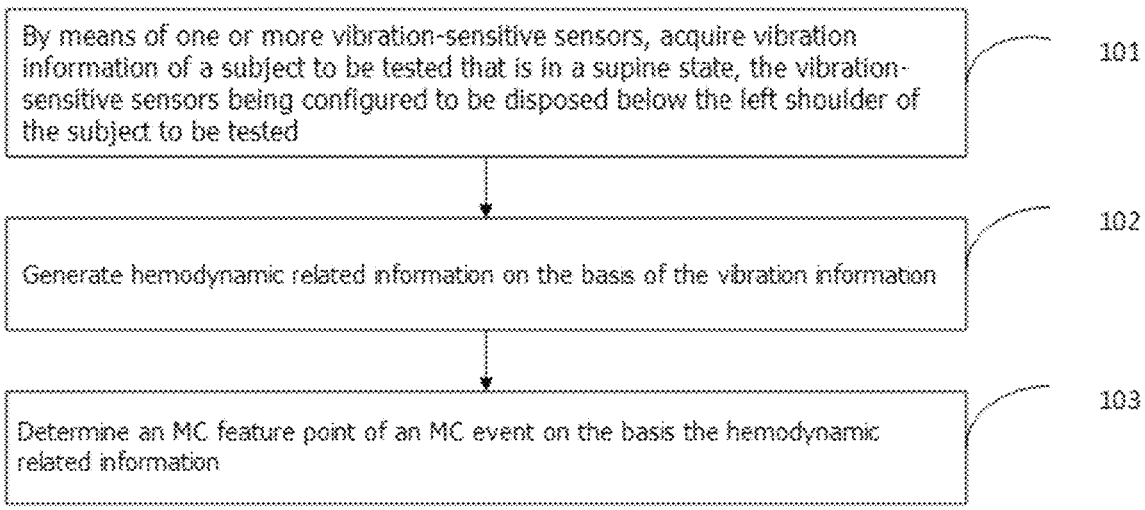
FIG. 4 illustrates a flowchart of a cardiac physiological parameter measuring method in accordance with the embodiment of the present invention.

As shown in FIG. 4, a cardiac physiological parameter measuring method 100 comprises the following steps:

step 101: acquiring vibration information of a subject to be tested in a supine state by means of one or more vibration sensors; wherein the one or more vibration sensors are configured to be disposed below the left shoulder of the subject to be tested; when the vibration sensor is disposed below the left shoulder of the subject to be tested, the vibration information acquired by the vibration sensor may include: vibration information caused by breathing, body vibration information caused by contraction and relaxation of the heart, body vibration information caused by blood vessel wall deformation, and human body movement information(body movement information). Body vibration information caused by contraction and relaxation of the heart can include body vibration information caused by the contraction and relaxation of the heart itself, as well as body vibration information caused by blood flow caused by contraction and relaxation of the heart, such as body vibration information caused by blood flowing in the aortic arch due to heart's ejection. Body vibration information caused by blood vessel wall deformation, can be caused by pulse wave propagating along blood vessels, where heart's ejection causes the aortic wall to expand to form a pulse wave. The body movement information can be caused by the body movement such as leg bending, leg raising, turning over, shaking, etc. Specifically, breathing will cause the whole body, especially the body sections corresponding to the thorax and abdomen, to vibrate rhythmically. The contraction and relaxation of the heart will also cause the whole body, especially the body around the heart, to vibrate. The left ventricle pumps blood to the aorta, the blood will push against the aortic arch at the moment; and the heart itself and the connected large blood vessels as a whole will also undergo a series of movements. The farther the body part is from the heart, the weaker the vibration will be.

Figure 5:
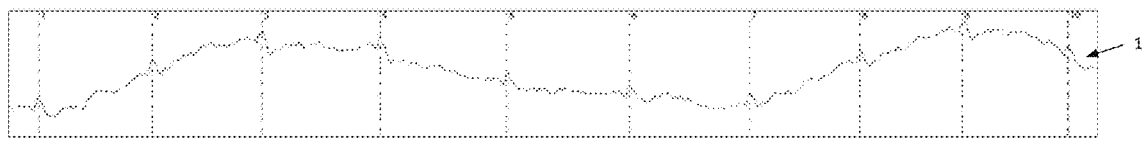
FIG. 5 illustrates a waveform graph of the vibration information in the cardiac physiological parameter measuring method in accordance with the embodiment of the present invention.

Specifically, FIG. 5 shows the waveform graph of the acquired vibration information of the left shoulder of the subject to be tested. Graph 1 is the waveform diagram of the vibration information acquired by the vibration sensor, where the horizontal axis represents time, and the vertical axis represents the normalized vibration information, which is dimensionless.

Specifically, the vibration sensor is configured to be disposed below the left shoulder blade of the subject to be tested. And the sensing area of the vibration sensor covers the shoulder area corresponding to the left shoulder blade of the subject to be tested.

Step 102: generating hemodynamic related information on the basis of the vibration information;

specifically, "generating hemodynamic related information on the basis of the vibration information" in step 102, comprises:

generating hemodynamic related information by preprocessing the vibration information, where the preprocessing comprises at least one of: filtering, denoising, and signal scaling. For example, in one embodiment, filtering the vibration information below 1 Hz, by means of but not limited to one or more of: low-pass filtering, band-pass filtering, IIR (Infinite Impulse Response) filtering, FIR (Finite Impulse Response) filtering, wavelet filtering, zero-phase bidirectional filtering, and polynomial fitting and smoothing filtering. The vibration information can be filtered at least once. If the vibration information carries power frequency interference, a power frequency filter can used to filter power frequency noise. Some high-frequency noise (for example, above 45 Hz) can also be filtered. The processed information can be scaled according to the situation to obtain hemodynamic related information.

Figure 6:
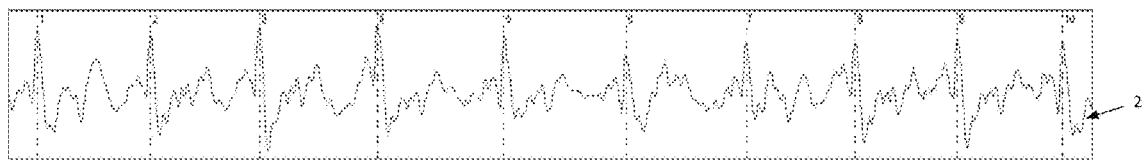
FIG. 6 illustrates a waveform graph of the hemodynamic related information in the cardiac physiological parameter measuring method in accordance with the embodiment of the present invention.

As shown in FIG. 6, graph 2 is a waveform diagram of hemodynamic related information generated on the basis of the vibration information, where the horizontal axis represents time. Specifically, graph 2 is the hemodynamic related information generated by filtering, denoising, signal scaling and other processing on graph 1.

Step 103: determining an MC feature point of an MC event on the basis the hemodynamic related information.

Specifically, step 103 can be implemented in several different ways:

first way: graphically displaying the hemodynamic related information;

determining a point of manual calibration on the graphical display interface; and setting the point as the MC feature point of the MC event.

Specifically, in one embodiment, the waveform graph of the hemodynamic related information can be displayed on the display, for example, so that the calibrating operator (such as a doctor, a professionally trained operator) can perform calibration on the waveform, and the calibrated point is the MC feature point of the MC event.

In a specific embodiment, the graphical display interface may have a preset zoom display function, when manually calibrating points, the calibrating operator may zoom in the graphical display interface of hemodynamic related information to determine MC feature points. The waveform graph of the hemodynamic related information can also be set with different filter intervals, for example, any filter interval between 1-45 HZ can be set. The filter frequency interval can be different according to the actual situation, such as an interval of 1-20 HZ, an interval of 1-30 HZ, an interval of 1-35 HZ, an interval of 1-40 HZ, an interval of 2-20 HZ, an interval of 2-20 HZ, and an interval of any sub-range within 1-45 HZ, etc., for example, can also be an interval of 3-20 HZ, 3-21 HZ, 3-40 HZ, 3-25 HZ, 3-45 HZ, 5-20 HZ, 5-26 HZ, 5-40 HZ, or 5-45 HZ, and so on. The calibrating operator can independently select a filter interval according to the detail display of the waveform graph of the hemodynamic related information, so as to obtain more detailed hemodynamic related information by filtering, and calibrate the feature point. The manually calibrated point needs to be on the wave graph or with a distance less than a preset value from the wave graph, so as to avoid the point generated by false touch (such as the touch point caused by hand shaking) being set as the manually calibrated point. During the process, the operation of setting the current manually calibrated point as the MC feature point of the MC event will be performed only after the calibrating operator further confirm.

Further, in order to prompt the calibrating operator to perform the calibration operation, prompt information may also be displayed on the graphic display interface; wherein the prompt information is used to prompt manual calibration of MC feature points of the MC event.

Second way: determining an MC feature point of an MC event from the hemodynamic related information on the basis of a feature search. The features in the feature search can include, but not limited to, peaks, valleys, wave widths, amplitudes, the maximum value of the function, the minimum value of the function, maximums, minimums, etc.

Specifically, the step of determining an MC feature point of an MC event from the hemodynamic related information on the basis of a feature search, comprises the following steps of: extracting high-frequency component from the hemodynamic related information to obtain a high-frequency component signal waveform graph; and performing a feature search on the high-frequency component signal waveform graph to determine the MC feature point of the MC event.

In some embodiments, the vibration sensor is a fiber-optic sensor, and the fiber-optic sensor is sensitive to changes in vibration displacement or pressure changes caused by changes in vibration displacement. Vibration information essentially corresponds to the acceleration change information, speed change information, and displacement change information. The information of changes in displacement is relatively smooth. Some changes of acceleration or speed are difficult to identify in the information of changes in displacement. For example, the speed gradually increases from 0 to a certain peak, and then gradually decreases from the peak to 0, the speed change graph forms a waveform that first rises and then drops, but the displacement change graph is a monotonous waveform. Therefore, compared to the signal component corresponding to the displacement, the peak-to-valley time width of the signal component corresponding to the speed or acceleration is narrower, which may be called high-frequency component information. The time of one cardiac cycle of systole and diastole is usually about 0.8 seconds. The information about the opening and closing of the heart valve in the period belongs to the high-frequency component information. Therefore, it is necessary to extract the feature of the corresponding event by high-frequency component extraction such as second-order differentiation. In other embodiments, the vibration sensor may be an acceleration sensor, and the vibration information acquired by the acceleration sensor contains relatively high frequency signal features. The feature search method can be used directly to determine the MC feature point of the MC time. In order to better highlight detailed features, it is also possible to perform higher frequency information component extraction processing to determine the MC feature points of MC events. Specifically, the step of "extracting high-frequency components of the hemodynamic related information", comprises:

extracting high-frequency component from the hemodynamic related information by means of polynomial fitting and smooth filtering.

More specifically, differential processing such as a second-order differential processing or a fourth-order differential processing is one of the methods for extracting high-frequency component.

Third way: when the vibration sensor is a fiber-optic sensor, on the basis the hemodynamic related information generated by the vibration information acquired by the optical fiber sensor, the step of determine the MC feature point of the MC time can further comprise the following steps of:

performing second-order differential processing and fourth-order differential processing on the hemodynamic related information to generate a second-order differential graph and a fourth-order differential graph, respectively;

setting the highest peak in one cardiac cycle of the second-order differential graph as an auxiliary feature point;

synchronizing the second-order differential graph and the fourth-order differential graph on the same time axis, and determining a time point on the fourth-order differential graph corresponding to the auxiliary feature point on the second-order differential graph; and determining the first valley on the fourth-order differential graph before the time point in the same cardiac cycle as the MC feature point of the MC event.

Specifically, the vibration sensor obtains waveform in a continuous time, including data of several cardiac cycles, the total waveform in the graph need to be divided into cardiac cycles by means of the following method:

performing peak search on the signal waveform corresponding to hemodynamic related information; and setting the time interval corresponding to the waveform between the two adjacent highest peaks as one cardiac cycle.

Specifically, for example, a peak search may be performed on graph 2, and the waveform between the highest peak and the next highest peak is taken as one cardiac cycle, as shown in FIG. 6.

Figure 7:
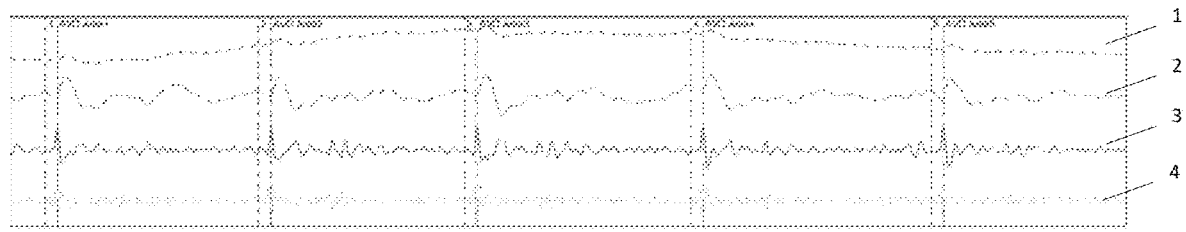
FIG. 7 illustrates multiple waveform graphs generated after processing the first hemodynamic related information in the cardiac physiological parameter measuring method in accordance with the embodiment of the present invention.

Specifically, as shown in FIG. 7, graph 2 is the waveform of the hemodynamic related information in step 102, and graph 3 is the waveform graph of graph 2 after second-order differentiation processing. In one cardiac cycle, perform a peak search on graph 3, and the highest peak in the cardiac cycle is the auxiliary feature point.

Figure 8:
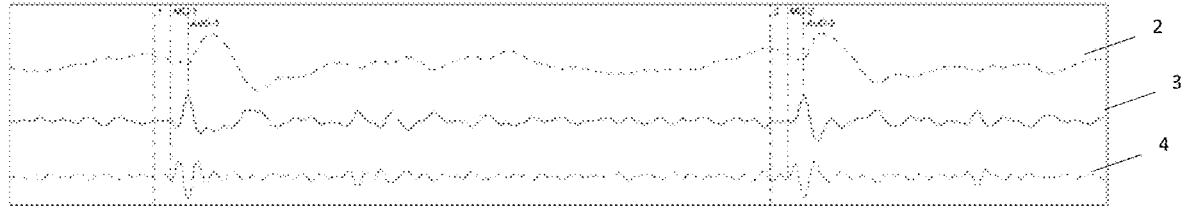
FIG. 8 is a partial enlarged schematic diagram of multiple waveform graphs in FIG. 7.

As shown in FIG. 8, FIG. 8 is an enlarged display view of a waveform including one complete cardiac cycle selected from FIG. 7. Graph 4 is the waveform graph after the fourth-order differential processing on graph 2. The graph 4 and graph 3 are placed on the same time axis for synchronization, and the time point corresponding to the auxiliary feature point on graph 2 is determined on graph 4; In the same cardiac cycle, the first valley on graph 4 before the time point is taken as the MC feature point of the MC event.

In some embodiments, the cardiac physiological parameter measuring method 100 may further comprises a step of: determining an AVO feature point of an AVO event on the basis the hemodynamic related information.

Specifically, the step of "determining an AVO feature point of an AVO event on the basis the hemodynamic related information" can be performed in a variety of ways:

first way: graphically displaying the hemodynamic related information; and displaying prompt information on the graphical display interface; wherein the prompt information is used to prompt manual calibration of the AVO feature point of the AVO event;

determine the point of manual calibration on the graphical display interface; and setting the point as the AVO feature point of the AVO event.

Specifically, similar to the manual calibration of the MC feature points of the MC event, the AVO feature point of the AVO event can also be manually calibrated.

Second way: performing second-order differential processing on the hemodynamic related information to generate a second-order differential graph; and determining the highest peak in one cardiac cycle of the second-order differential graph as the AVO feature point of the AVO event (also being the auxiliary feature point described above in the third way of determining an MC feature point).

Specifically, as shown in FIG. 8, graph 3 is the waveform graph of graph 2 after second-order differentiation processing. In one cardiac cycle, perform a peak search on graph 3, and the highest peak in the cardiac cycle is the AVO feature point of the AVO event.

There is a small time delay between the time of the actual occurrence of the MC event or AVO event and the time of the vibration sensor capturing the event. This time delay can be ignored in the subsequent IVCT calculations, or a correction coefficient can be assigned to the measured IVCT.

In some embodiments, after determining the MC feature point and the AVO feature point, the cardiac physiological parameter measurement method 100 may further comprise a step of:

determining IVCT on the basis of the time points corresponding to the MC feature point and the AVO feature point in the same cardiac cycle.

After determining the MC feature point and AVO feature point, selecting time points of MC and AVO within one cardiac cycle, namely MCT (Mitral Valve Closure Time), AVOT (Aortic Valve Opening Time), and then determined IVCT according to the following formula:

$$IVCT=AVOT-MCT;$$

specifically, in one embodiment, the step of "determining IVCT on the basis of the time points corresponding to the MC feature point and the AVO feature point in the same cardiac cycle" further comprises steps of:

determining MC time points corresponding to MC feature points and AVO time points corresponding to AVO feature points in multiple cardiac cycles;

determining the IVCT in each cardiac cycle on the basis of the MC time point and the AVO time point in the same cardiac cycle; and averaging the IVCT in each cardiac cycle to obtain the final IVCT.

The methods of dividing the cardiac cycles can be in the following ways:

first way: performing peak search on the signal waveform corresponding to hemodynamic related information; and setting the time interval corresponding to the waveform between the two adjacent highest peaks as one cardiac cycle.

In other embodiments, other methods can be used to determine the cardiac cycles, for example:

second way: while acquiring vibration information of a subject to be tested in a supine state by means of one or more vibration sensors, acquiring a synchronous monitoring electrocardiogram of the subject to be tested; where the specific synchronous monitoring electrocardiogram is ECG (Electrocardiograph); and determining the cardiac cycle on the basis of the synchronous monitoring electrocardiogram.

Specifically, the tester's ECG can be monitored simultaneously. Since the ECG has electrodes connected, the waveform is stable and clear, which can be used as a scale to divide cardiac cycles to determine the cardiac cycle.

In some embodiments, the cardiac physiological parameter measuring method 100 may further comprises steps of:

while acquiring vibration information of a subject to be tested in a supine state by means of one or more vibration sensors, acquiring PCG (Phonocardiogram) signals of the apex region of the subject to be tested;

determining the MC feature point of the MC event and the AVO feature point of the AVO event on the basis of the graph corresponding to the PCG signals; and using the MC feature point and/or AVO feature point obtained by the PCG signals to correct the MC feature point and/or AVO feature point obtained by the feature search method using the vibration information.

Specifically, the MC feature points and/or AVO feature points obtained on the basis of the graph corresponding to the PCG signals can also be used to correct the MC feature points and/or AVO feature points obtained on the basis the hemodynamic related information, so as to improve accuracy in complex environments.

In some embodiments, after determining the MC feature points, the AVO feature points, and the IVCT, the cardiac physiological parameter measurement method 100 may further comprises a step of: outputting one or more of: the information of the MC feature point, the information of the AVO feature point, and the IVCT. For example, the output device may be a display.

Specifically, the determined information of the MC feature points and/or the information of the AVO feature points and/or IVCT may be output according to needs or instructions.

In some embodiments, two vibration sensors can be placed on top of each other, and both are configured to be disposed below the left shoulder of the subject to be tested. The two vibration sensors work synchronously, and the vibration information obtained by one of the vibration sensors can be used to determine the MC feature point of the MC event, the vibration information obtained by the other vibration sensor can be used to determine the AVO feature point of the AVO event. In other embodiments, multiple vibration sensors can work simultaneously, and each vibration sensor can be independently used to determine MC feature points, AVO feature points, and IVCT, and then use the vibration information obtained by multiple vibration sensors to verify each other to identify and eliminate some unreasonable information.

The above is the description of the method. For the information acquisition device, the information acquisition device may also include a human body auxiliary positioning device; the human body auxiliary positioning device is used to assist in restricting the subject to be tested so that different preset section of the subject to be tested correspond to the vibration sensors on the information acquisition device.

Specifically, in an embodiment, the human body auxiliary positioning device may include of one or more of the following: left shoulder block, right shoulder block, left foot block, right foot block, neck pillow, and body contour.

Figure 9:
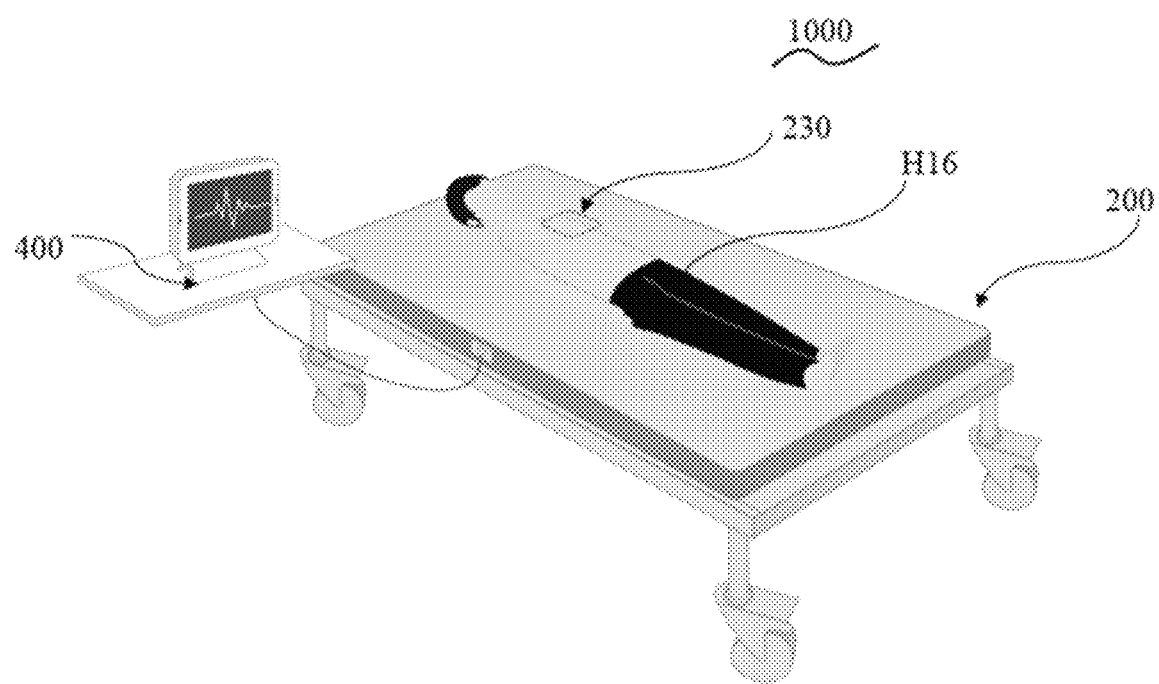
FIG. 9 is a schematic diagram of the information acquisition device in a used state for the cardiac physiological parameter measuring method in accordance with the embodiment of the present invention.

As shown in FIG. 9, the cardiac physiological parameter measurement device 1000 includes an information acquisition device 200 and a data display device 400. The information acquisition device 200 is a mattress. The measured subject H16 lies on the mattress with the back facing the mattress. A vibration sensor 230 is provided on the mattress at a position corresponding to the left shoulder blade on the back of the measured subject. The vibration sensor 230 is used to collect vibration signals from the shoulder section of the subject H16 to be tested. The sensing area of the vibration sensor at least covers the back section corresponding to the left scapula of the subject H16 to be tested. The sensing area of a vibration sensor refers to the region where the vibration sensor actually senses vibration. For example, when the vibration sensor is a fiber-optic sensor, the sensing area refers to the area where the optical fiber is distributed in the fiber-optic sensor. The output device such as the data display device 400 is used to display the acquired signals. The data display device 400 may be one or more of: a display, a mobile phone, a tablet computer, a projector, a wearable device (watch, earphone, glasses, etc.), a braille display, etc. The display output mode may be one or more of: a graphic display, a digital display, voice broadcast, braille display, etc. Further, the data display device 400 may include a printer for printing related data and analysis reports.

Figure 10:
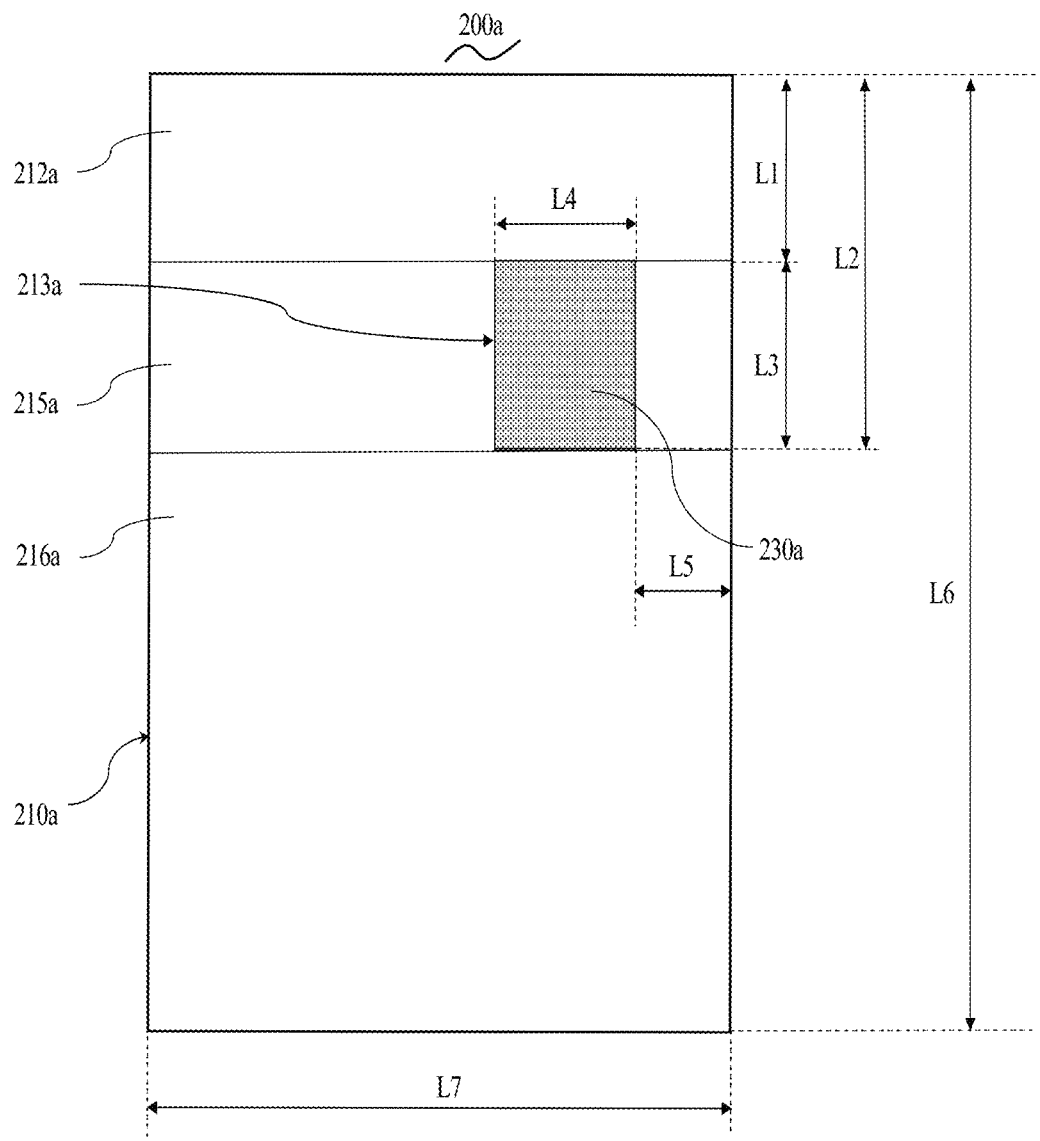
FIG. 10 is a schematic structural diagram of an information acquisition device in accordance with the embodiment of the present invention.

Mattress Embodiment 1:

Referring to FIG. 10, an embodiment of the information acquisition device 200 is a mattress 200a, and FIG. 10 is a schematic top view of the mattress 200a. The mattress 200a includes a main body 210a and a left shoulder vibration sensor 230a mounted on the main body 210a. The left shoulder vibration sensor 230a is disposed on the upper left side of the main body 210a and corresponds to the position of the left shoulder blade on the back of the subject.

The main body 210a includes a head region 212a and a back region 216a. The head region 212a is located at the front of the main body 210a. The head region 212a corresponds to the position of the head of the measured subject and is used for the head of the measured subject to lean against. The back region 216a is located at the rear of the head region 212a and corresponds to the back position of the measured subject, and is used for the back of the measured subject to lean against.

The back region 216a includes a shoulder region 215a, the shoulder region 215a is located at the front of the back region 216a and adjacent to the head region 212a, and the shoulder region 215a is used for the shoulder of the measured subject to abut against, the shoulder region 215a includes a first position 213a. The first position 213a is located on the left side of the shoulder region 215a and corresponds to the position of the left shoulder blade on the back of the measured subject. The left shoulder vibration sensor 230a is installed at the first position 213a. When the measured subject lies on the mattress 200a (his back faces the mattress), the shoulder of the measured subject pressed against the left shoulder vibration sensor 230a, thus the left shoulder vibration sensor 230a can acquires the vibration signal of the measured subject's shoulder. The main body 210a may have a leather case on which a pocket is provided, and the left shoulder vibration sensor 230a is installed in the pocket.

The main body 210a is rectangular, with a length L6 of 1850 mm and a width L7 of 850 mm. The shoulder region 215a is rectangular, the distance L1 between the top edge of the shoulder region 215a and the top edge of the main body 210a is 398 mm, the length L3 of the shoulder region 215a is 244 mm, and the width is the same as that of the main body 210a. The first position 213a is rectangular, its length is the same as the shoulder region 215a, and the width L4 is 159 mm. The distance L1 between the top edge of the first position 213a and the top edge of the main body 210a is 398 mm, and the distance L2 between the bottom edge of the first position 213a and the top edge of the main body 210a is 642 mm. The distance L5 between the left side of the first position 213a and the left side of the main body 210a is 205 mm. The shape and size of the left shoulder vibration sensor 230a are consistent with the first position 213a.

The dimensions of the mattress in this embodiment, namely the values of L1, L2, L3, L4, L5, L6, and L7, are very appropriate for those subjects whose height is in the range of 155 cm~188 cm and the shoulder width is in the range of 38 cm~50 cm.

In other embodiments, the dimensions L1, L2, L3, L4, L5, L6, and L7 may be adjusted by a certain size such as ±5 mm according to the body shape of the subject to be tested on the basis of the above-mentioned sizes in this embodiment.

In other embodiments, the information acquisition device 200 may include a vibration sensor. The vibration sensor is a fiber-optic sensor. The fiber-optic sensor is encapsulated to form a cuboid with a width of 100 mm-200 mm, a length of 200 mm-290 mm, and a thickness of 1 mm or more. The information acquisition device 200 is configured to be disposed below the left shoulder blade of the subject to be tested. In other embodiments, the shape of the information acquisition device 200 may also be a cross-sectional shape of the left shoulder blade of the human body lying on the back, so that the information acquisition device 200 can cover the left shoulder blade of the subject to be tested when being placed under the left shoulder of the subject to be tested.

In other embodiments, the left shoulder vibration sensor may also have other shapes, such as a circle, an ellipse, and a triangle.

Figure 11:
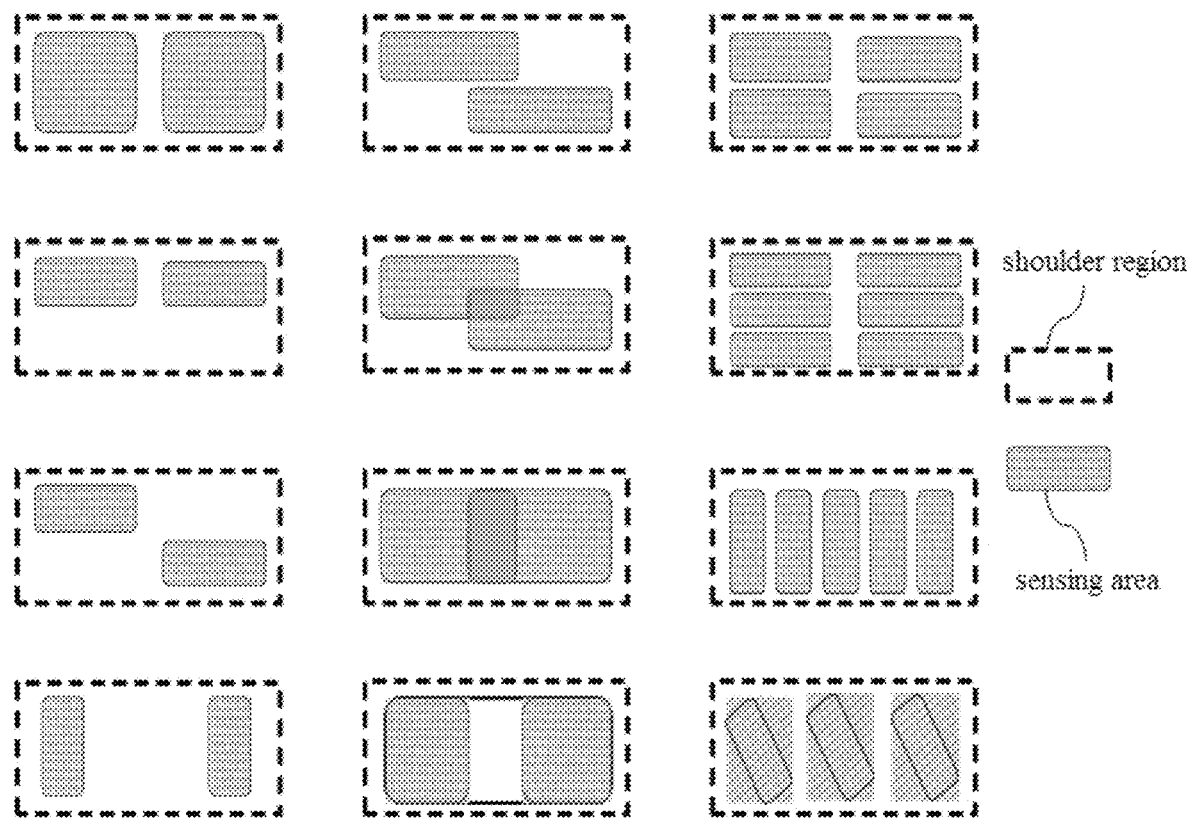
FIG. 11 is a schematic diagram illustrating different vibration sensors in the information acquisition device with different arrangements below the shoulder region according to an embodiment of the present invention.

The position of the left shoulder vibration sensor on the main body can be adjusted within a certain range on the basis of this embodiment; there may be multiple vibration sensors, and the signal transmissions of multiple different vibration sensors are independent of each other; the sensing area of each vibration sensor can correspond in whole or in part to the position of the left shoulder blade of the measured subject, which are all within the protection scope of this invention. As shown in FIG. 11, shoulder regions are represented with dotted lines, and sensing areas of the vibration sensors are represented with shade. In some embodiments, multiple vibration sensors can also be implemented by means of only one vibration sensor which has multiple sensing areas as shown in FIG. 11.

Figure 12:
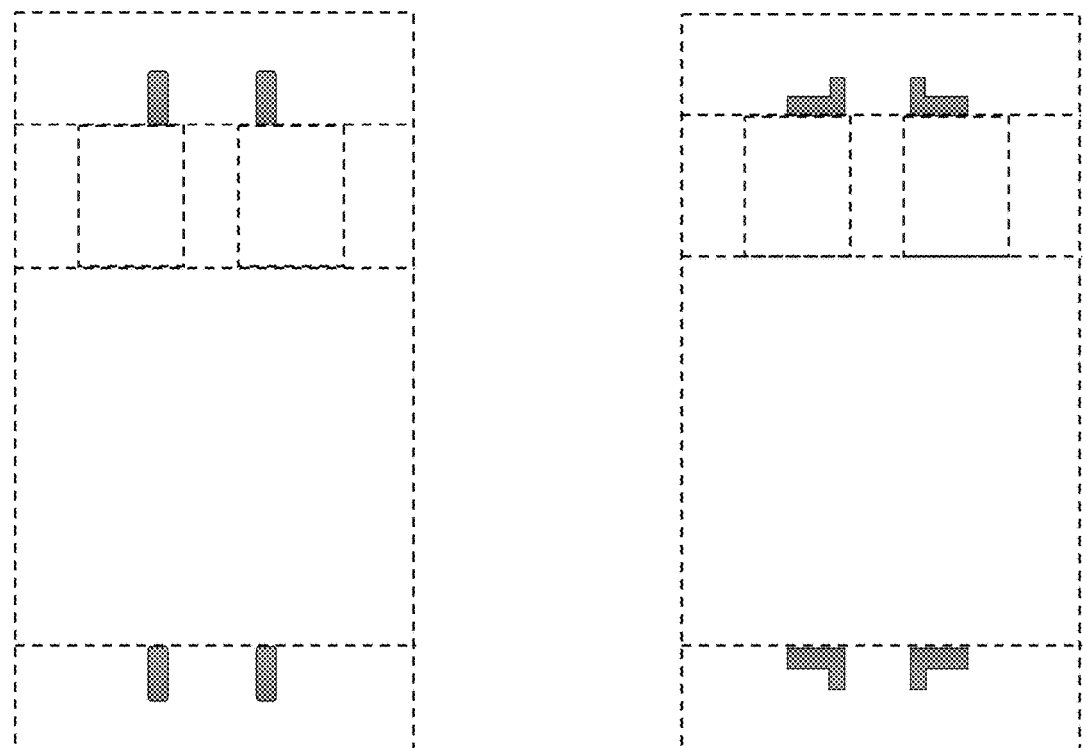
FIG. 12 is a schematic diagram of an auxiliary positioning device in the information acquisition device according to an embodiment of the present invention.

In other embodiments, the positions, shapes, and dimensions of the blocks can be changed or adjusted within a certain range, as long as making vibration sensors roughly corresponding to the position of the shoulder blade of the measured subject when lying on the back, and restricting the measured subject from moving significantly during the measurement process, thereby reducing the measurement error, and not render the measured subject a strong discomfort. The vibration sensors are shown with shade in FIG. 12.

Figure 13:
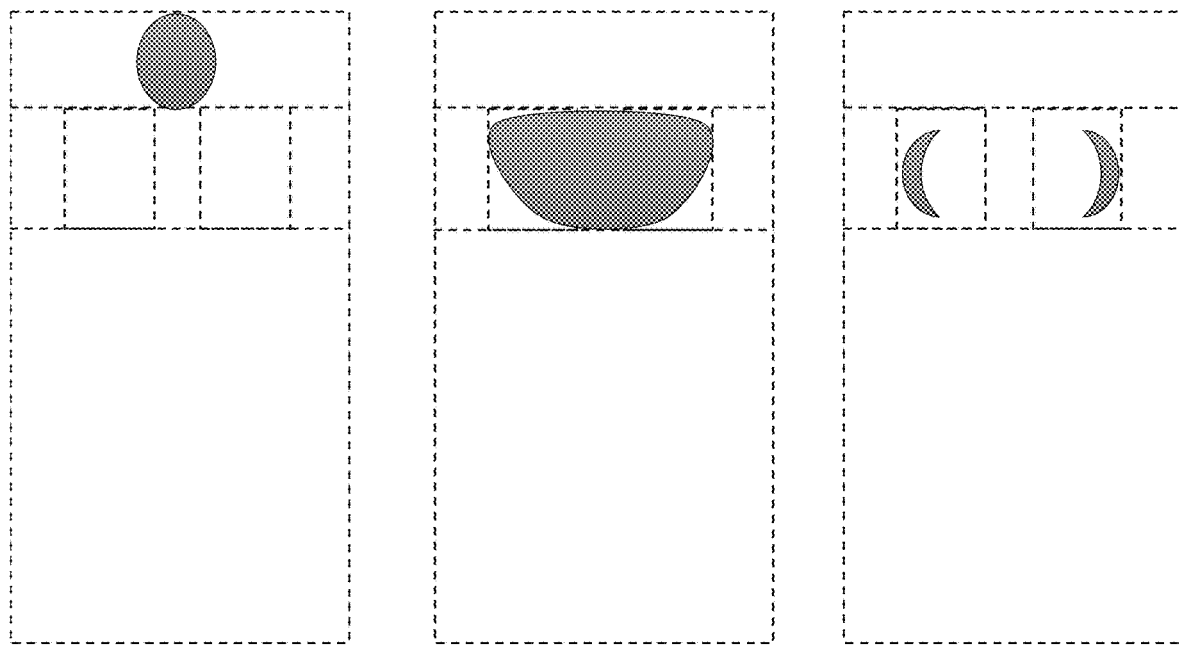
FIG. 13 is a schematic diagram of the auxiliary positioning device in the information acquisition device according to an embodiment of the present invention.

In other embodiments, depressions can be used to limit the positions of the head and shoulders of the measured subject when lying on the back. As shown in FIG. 13, the shaded parts in the figure represent the depressions in the mattress, and these depressions are set in the head region, back region or shoulder region used for the measured subject's head, back, and shoulders to abut against. These depressions can not only ensure that the position of the shoulder blade roughly corresponds to the vibration sensor when the measured subject is lying on the back, but also can provide a mattress structure according to ergonomics that can make the measured subject feel comfortable and natural, and thus improve the user experience.

Figure 14:
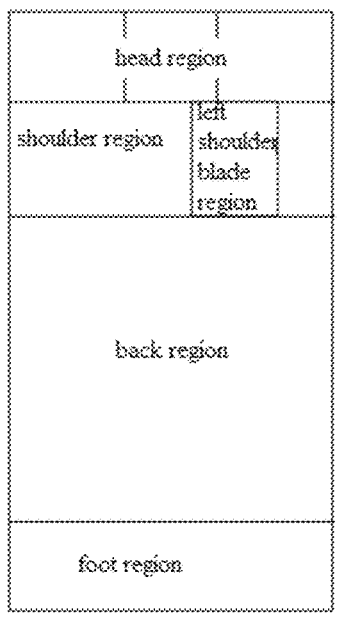
FIG. 14 illustrates regional distribution of the information acquisition device in accordance with an embodiment of the present invention.
Figure 14:
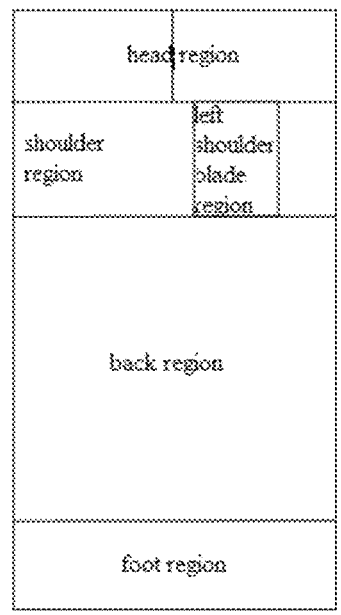
Figure 14:
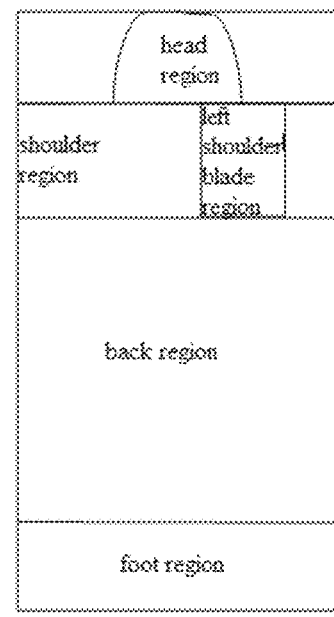

In other embodiments, it is also possible to mark the relevant location region on the mattress using marking lines or marking text to indicating the position of the measured subject lying on the mattress, so as to ensure that the scapula of the measured subject corresponds to the vibration sensor. As shown in FIG. 14, the information acquisition device can include a head region (which can be identified in various ways), a shoulder region (the shoulder region can include the left shoulder blade region), a back region, and a foot region; the different regions are respectively corresponding to a body section of the measured subject. Specifically, the head region corresponds to the human head, and the shoulder region corresponds to the human shoulder. Furthermore, the left shoulder blade region corresponds to the left scapula of the human body (in some embodiments, the left shoulder blade region can also be named the first position); the back region corresponds to the back section of the human body, and the foot region corresponds to the foot of the human body. In addition, in actual applications, the names of each region can be flexibly adjusted as needed, such as the head region can also be named the first region.

In other embodiments, the vibration sensor does not need to be fixed at the left shoulder position, and the sensors in the mattress can be designed as a movable structure. When the subject to be tested lies supine on the mattress, the position of the vibration sensor can be flexibly adjusted according to the position of the scapula of the measured subject, so that the vibration sensor corresponds to the scapula of the measured subject.

In other embodiments, the vibration sensor may be an acceleration sensor, a speed sensor, a displacement sensor, a pressure sensor, a strain sensor, a stress sensor, or sensors (such as electrostatic sensors, inflatable micro-motion sensors, radar sensors, etc.) that convert physical quantities equivalently based on acceleration, speed, displacement, or pressure. The strain sensor may be a fiber-optic strain sensor.

Figure 15:
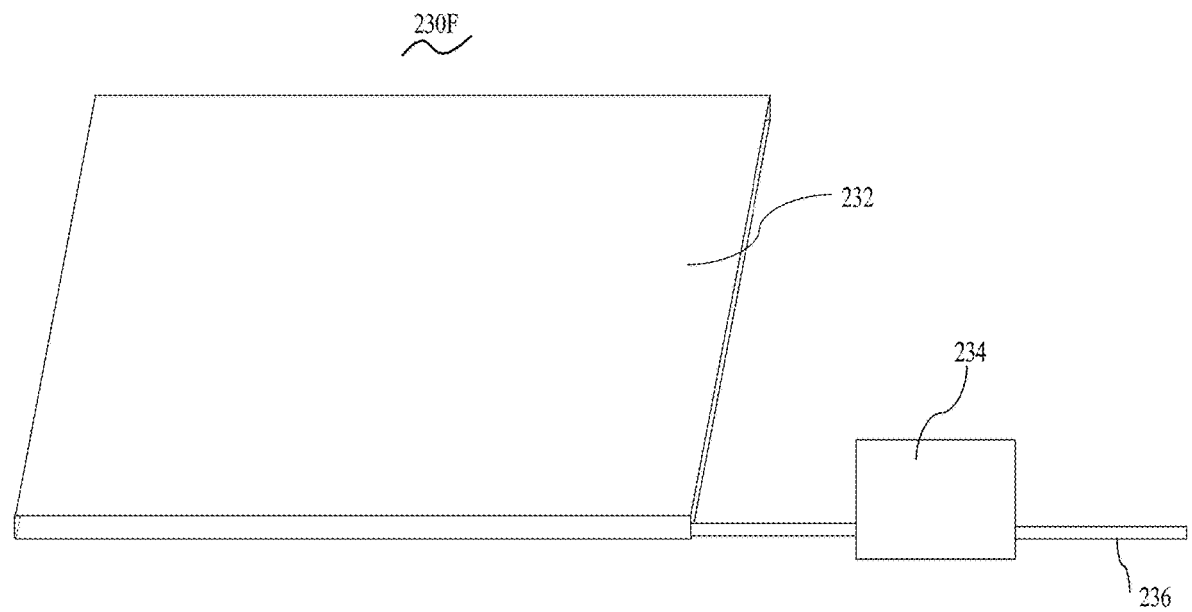
FIG. 15 is a structural block diagram of a fiber-optic sensor in the information acquisition device in accordance with an embodiment of the present invention.

In some embodiments of this invention, the vibration sensor 230a as shown in FIG. 10 may be a fiber-optic sensor 230F, referring to FIG. 15, the fiber-optic sensor 230F includes a sensor pad 232, a control box 234, and a communication line 236.

Figure 16:
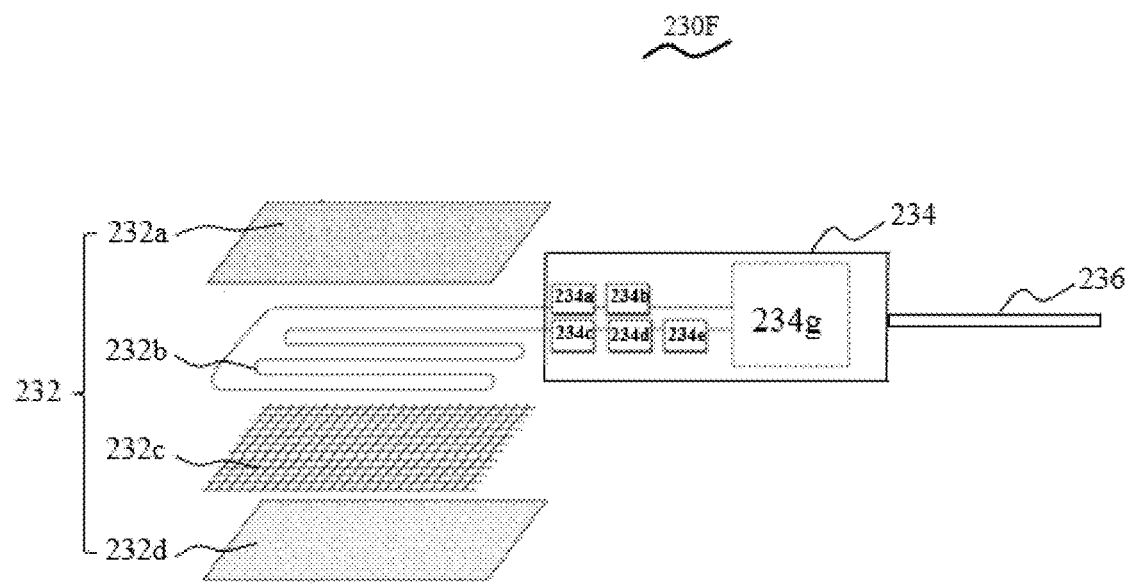
FIG. 16 is an exploded schematic diagram of the fiber-optic sensor in the information acquisition device according to an embodiment of the present invention.

FIG. 16 is an exploded view of the structure of the fiber-optic sensor 230F. The sensor pad 232 includes an upper cover 232a, an optical fiber layer 232b, a mesh layer 232c, and a lower cover 232d from top to bottom. The upper cover 232a and the lower cover 232b are made of silicone materials, and sandwich both the optical fiber layer 232b and the mesh layer 232c therebetween to protect the optical fiber as well as disperse external force so that the external force is dispersed along the force application point.

The optical fiber layer 232b may be a serpentine structure or a looped structure. The looped structure is formed by one optical fiber arranged into a plurality of loops disposed in one plane; each loop can form a substantially parallelogram structure (such as a rectangle, a square, etc.) with rounded edges and without sharp bends. In other embodiments, the looped structure may be circular or elliptical. In other embodiments, the looped structure may also form an irregular shape without sharp bends.

The mesh layer 232c is made of any suitable material with through openings arranged in a repeating pattern. In other embodiments, the mesh layer is formed of woven fibers, such as polymer fibers, natural fabric fibers, composite fabric fibers, or other fibers. In other embodiments, the upper cover 232a and the lower cover 232b may also be made of flexible materials, or may be integrated together. In other embodiments, the fiber-optic sensor 230F may further include an outer case, which is made of waterproof and protective material, and wraps the upper cover 232a, the optical fiber layer 232b, the mesh layer 232c, and the lower cover 232d into one integral body. In other embodiments, the sensor pad 232 may further include a support structure, which may be a rigid structure, such as a stiff cardboard, hard plastic board, wood board, etc. The support structure may support the optical fiber layer 232b, and can make deformation of the optical fiber layer rebound faster when an external force applied to the optical fiber layer 232b, so the optical fiber layer can obtain high-frequency signals.

The control box 234 includes a light source 234a, a light source driver 234b, a receiver 234c, an amplifier/filter circuit 234d, an analog-to-digital conversion module 234e, and a control processing module 234g. One end of the optical fiber layer 232b is connected to the light source 234a. The light source 234a may be an LED light source. The light source 234a is connected to the light source driver 234b. The light source driver 234b is used to control switch and energy level of the light source. The other end of the optical fiber layer 232b is connected to the receiver 234c. The receiver 234c is used to receive optical signals transmitted through the optical fiber layer 232b. The receiver 234c is connected to the amplifier/filter circuit 234d, and the amplifier/filter circuit 234d is connected to the analog-to-digital converter 234e.

The amplifier/filter circuit 234d is used to filter the signal. In this embodiment, the amplifier/filter circuit 234d comprises an AC coupling circuit and a low-pass filter circuit. In other embodiments, other bandpass filter circuits may also be used for filter processing.

The analog-to-digital converter 234e is used to convert the received optical signals into digital signals. The light source driver 234b and the analog-to-digital converter 234e are connected to the control processing module 234g. The control processing module 234g is used to control the light source driver 234b to drive the light source 234a to emit light.

When the fiber-optic sensor 230F is placed under the body of the subject to be tested, the subject to be tested applies an external force to the fiber-optic sensor 230F, the mesh layer 232c can disperse the external force that would otherwise be applied to a certain force application point on the optical fiber, to the optical fiber around the force application point. The optical fiber layer 232b may generate micro bending, which causes changes in the parameter (such as intensity) of light transmitted through the optical fiber layer 232b. The receiver 234c can receive the changed light, and changes in light can be processed and calculated by the control processing module 234g. The bending amount of the optical fiber layer 232b depends on the applied force, the diameter of the optical fiber, the diameter of the mesh fiber weaving the mesh layer, and the size of the openings in the mesh layer. By balancing these parameters of the diameter of the optical fiber, the diameter of the mesh fiber, and the size of the openings in the mesh layer, when the external office is applied, different bending amount of the optical fiber is available, so that the fiber-optic sensor 230F has different sensitivity..

In this embodiment, the control box 234 is installed at the edge of the mattress. In other embodiments, the control box 234 may be further integrated with the data display device 400 as a whole.

In other embodiments, the five modules of the light source driver 234b, the receiver 234c, the amplifier/filter circuit 234d, the analog-to-digital conversion module 234e, and the control processing module 234g can be combined into one single module to perform all functions.

The communication line 236 is an electric wire used to connect the control box 234 and the data display device 400 for data communication. In other embodiments, the communication line 236 may be a wireless communication module, which may be integrated into the control box 234, the wireless communication module may be one of: a WIFI module, a Bluetooth module, an NB-IOT module, 2G 3G 4G and 5G modules.

To illustrate the advantages of some embodiments of this invention, the following device is used for acquiring signal:
the information acquisition device comprises: mattress 200a; left shoulder vibration sensor 230a using fiber-optic sensor; and information display device: a display.

Generally, in order to ensure the quality of the acquired signal, the measuring process needs the subject to be tested is in a quiet state.

Figure 17:
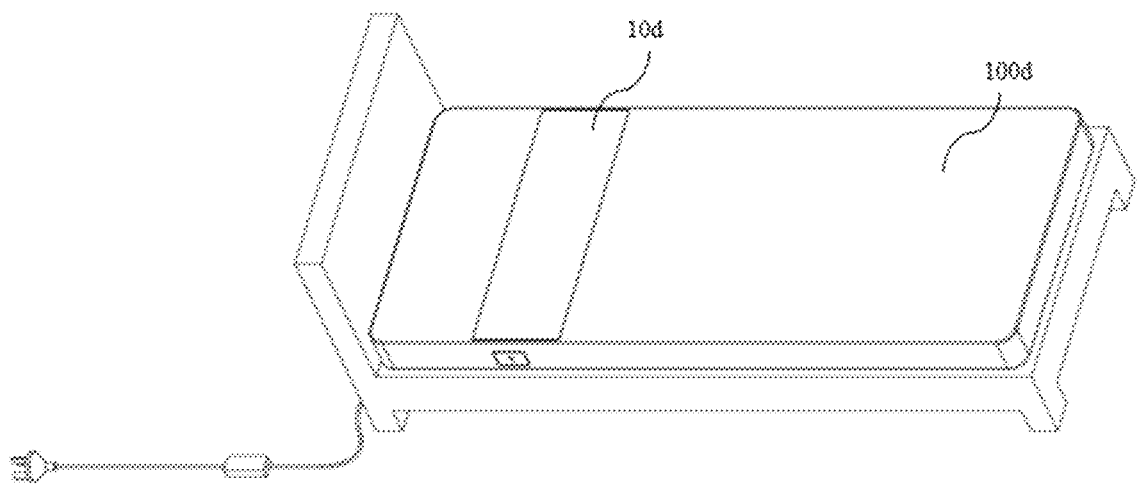
FIG. 17 is a schematic diagram of the information acquisition device according to an embodiment of the present invention.

In another specific embodiment, the information acquisition device may also, as shown in FIG. 17, comprise: a mattress 100d and a vibration sensor 10d arranged on the mattress 100d. The vibration sensor 10d covers the entire regions corresponding to the back of the human body on the mattress 100d.

Embodiment 2

Figure 18:
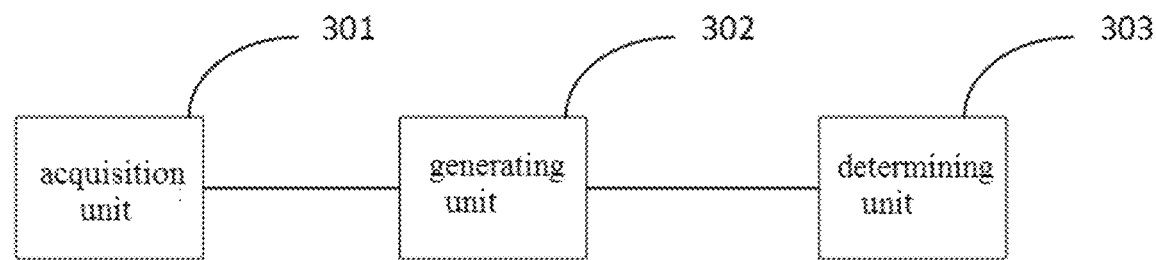
FIG. 18 is a structural block diagram of a cardiac physiological parameter measurement device in accordance with an embodiment of the present invention.

Embodiment 2 of the present invention further provides a cardiac physiological parameter measuring device. As shown in FIG. 18, the device includes:
- an acquisition unit 301, for acquiring vibration information of a subject to be tested in a supine state by means of one or more vibration sensors; wherein the one or more vibration sensors are configured to be disposed below the left shoulder of the subject to be tested;
- a generating unit 302, for generating hemodynamic related information on the basis of the vibration information; and
- a determining unit 303, for determining an MC feature point of an MC event on the basis the hemodynamic related information.

Specifically, Embodiment 2 of the present invention also discloses other related technical features; please refer to the description of Embodiment 1.

Embodiment 3

Figure 19:
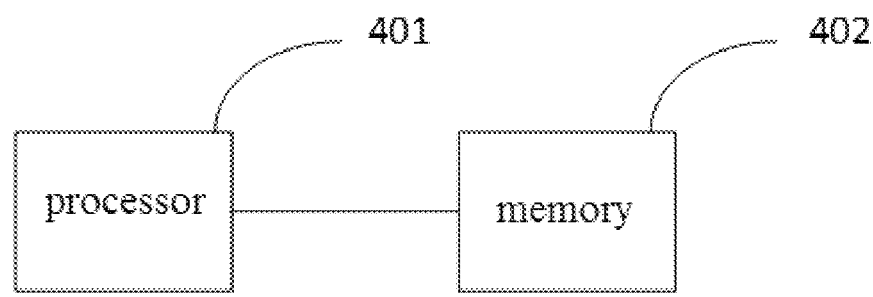
FIG. 19 is a structural block diagram of a terminal in accordance with an embodiment of the present invention.

Embodiment 3 of the present invention further discloses a terminal. As shown in FIG. 19, the terminal comprises:

a processor 401; and a memory 402 storing instructions executable by the processor;

wherein the processor 401 are used to perform:

acquiring vibration information of a subject to be tested in a supine state by means of one or more vibration sensors; wherein the one or more vibration sensors are configured to be disposed below the left shoulder of the subject to be tested;

generating hemodynamic related information on the basis of the vibration information; and determining an MC feature point of an MC event on the basis the hemodynamic related information.

Specifically, Embodiment 3 of the present invention also discloses other related technical features; please refer to the description of Embodiment 1.

Embodiment 4

Embodiment 4 of the present invention further discloses a computer storage medium that stores computer program, and the computer program are executed to perform the following processes:

process A: acquiring vibration information of a subject to be tested in a supine state by means of one or more vibration sensors; wherein the one or more vibration sensors are configured to be disposed below the left shoulder of the subject to be tested;

process B: generating hemodynamic related information on the basis of the vibration information; and process C: determining an MC feature point of an MC event on the basis of the hemodynamic related information.

Specifically, Embodiment 4 of the present invention also discloses other related technical features; please refer to the description of Embodiment 1.

Embodiment 5

Embodiment 5 of the present invention further provides a cardiac physiological parameter measuring system, comprising: one or more vibration sensors and an information processing device;

wherein the one or more vibration sensors are used for acquiring vibration information of a subject to be tested in a supine state, and are configured to be disposed below the left shoulder of the subject to be tested; and the information processing device is used for obtaining the vibration information collected by the one or more vibration sensors, generating hemodynamic related information on the basis of the vibration information; and determining an MC feature point of an MC event on the basis the hemodynamic related information.

Specifically, Embodiment 5 of the present invention also discloses other related technical features; please refer to the description of Embodiment 1. In addition, the vibration sensor in embodiment 5 of the present invention is consistent with the vibration sensor in embodiment 1, and the functions of the information processing device correspond to the method in embodiment 1.

Those skilled in the art can understand that the accompanying drawings are only schematic diagrams of preferred implementation scenes, and the modules or processes in the accompanying drawings may not be necessarily for implementing the present invention.

Those skilled in the art can understand that the modules in the device in the implementation scene above can be distributed according to the description above, or can be changed to be located in one or more devices in different implementation scenes. The modules of the above implementation scene can be combined into one module or further divided into multiple sub-modules.

The labels of the present invention are only for description, and do not represent the pros and cons of implementation scenes.

What has been disclosed above are only a few specific implementation scenes of the present invention, but the present invention is not limited thereto, and any changes that can be thought of by those skilled in the art should fall into the protection scope of the present invention.

What is claimed is:

1. A cardiac physiological parameter measuring method, comprising steps of:

acquiring vibration information of a subject to be tested in a supine state, comprising steps of:

providing a fiber-optic sensor including one optical fiber arranged in a pad and a control box connected with ends of the optical fiber;

connecting the control box of the fiber-optic sensor with a processor for data communication;

disposing the fiber-optic sensor under the back of the subject corresponding to the left shoulder of the subject, wherein a sensing area where the optical fiber is distributed in the fiber-optic sensor covers the back corresponding to the left shoulder blade of the subject; and micro body vibrations of the subject make the optical fiber micro bending;

processing and calculating, executed on a control processing module in the control box, changes in intensity of light passing through the optical fiber caused by the micro bending of the optical fiber; and obtaining, executed on the control processing module, vibration information on the basis of the changes in intensity of light; wherein the vibration information containing breathing vibration, body vibration caused by contraction and relaxation of the heart of the subject, body vibration information caused by blood vessel wall deformation, and body movement;

acquiring, executed on the processor, synchronous electrocardiogram (ECG) of the subject through an electrocardiogram sensor while acquiring vibration information;

communicating the vibration information from the fiber-optic sensor and the synchronous ECG from the electrocardiogram sensor to the processor;

normalizing, executed on the processor, the vibration information and obtaining a waveform of the vibration information, where the waveform has a horizontal axis representing time, and a vertical axis representing normalized vibration information, which is dimensionless;

preprocessing, executed on the processor, the waveform of the vibration information to generate a waveform of hemodynamic related information with peaks and valleys; comprising:

filtering the vibration information below 1 Hz and above 45 Hz;

dividing, executed on the processor, cardiac cycles on the basis of the synchronous ECG; and determining, executed on the processor, a Mitral Valve Closure (MC) feature point of an MC event on the basis of the waveform of the hemodynamic related information in one cardiac cycle; comprising steps of:

performing a second-order differential processing and a fourth-order differential processing on the waveform of the hemodynamic related information to generate a second-order differential graph and a fourth-order differential graph, respectively;

setting a highest peak in one cardiac cycle of the second-order differential graph as an auxiliary feature point;

synchronizing the second-order differential graph and the fourth-order differential graph on the horizontal axis representing time, and determining a time point of the fourth-order differential graph corresponding to the auxiliary feature point of the second-order differential graph; and determining a first valley on the fourth-order differential graph before the time point in the same cardiac cycle as the MC feature point of the MC event.

2. A non-transitory computer storage medium that stores computer program including a set of computer-executable instructions, wherein when the computer-executable instructions are executed by a processor, cause the processor to perform the cardiac physiological parameter measuring method of claim 1.

3. The cardiac physiological parameter measuring method of claim 1, further comprising an executing on the processor step of:

determining an Aortic Valve Opening (AVO) feature point of an AVO event on the basis of the waveform of the hemodynamic related information.

4. The cardiac physiological parameter measuring method of claim 3, wherein further comprising executing on the processor steps of:

while acquiring the vibration information of the subject to be tested in a supine state by means of the one or more vibration sensors, acquiring phonocardiogram (PCG) signals corresponding to an apex region of the subject to be tested;

determining the MC feature point of the MC event and/or the AVO feature point of the AVO event on the basis of a graph of the PCG signals; and using the MC feature point and/or AVO feature point obtained by the PCG signals to correct the MC feature point and/or AVO feature point obtained by a feature search on the waveform of the hemodynamic related information.

5. The cardiac physiological parameter measuring method of claim 3, wherein the control box comprises a light source, a light source driver, a receiver, an amplifier/filter circuit, an analog-to-digital conversion module, and the control processing module; one end of the optical fiber is connected to the light source, the light source is connected to the light source driver; the other end of the optical fiber is connected to the receiver, the receiver is used to receive optical signals transmitted through the optical fiber, the receiver is connected to the amplifier/filter circuit, the amplifier/filter circuit is connected to the analog-to-digital converter, the light source driver and the analog-to-digital converter are connected to the control processing module; and the control processing module is connected to the processor and a display for data communication.

6. The cardiac physiological parameter measuring method of claim 3, wherein the step of determining the AVO feature point of the AVO event is:

determining a highest peak in one cardiac cycle of the second-order differential graph as the AVO feature point of the AVO event.

7. The cardiac physiological parameter measuring method of claim 6, wherein, after the step of determining the AVO feature point of the AVO event, the method further comprises an executing on the processor step of:

determining an Isovolumetric Contraction Time (IVCT) on the basis of time points corresponding to the MC feature point and the AVO feature point in the same cardiac cycle.

8. The cardiac physiological parameter measuring method of claim 7, wherein the step of determining the IVCT further comprising executing on the processor steps of:

determining MC time points corresponding to MC feature points and AVO time points corresponding to AVO feature points in multiple cardiac cycles on the basis of the waveform of the hemodynamic related information;

determining the IVCT in each cardiac cycle on the basis of the MC time point and the AVO time point in the same cardiac cycle; and averaging the IVCT in each cardiac cycle to obtain a final IVCT.

9. The cardiac physiological parameter measuring method of claim 7, further comprising a step of:

outputting, executing on the processor, one or more of the AVO feature point, the MC feature point, and the IVCT to a display.

\* \* \* \* \*